(12) United States Patent
Jung et al.

(10) Patent No.: US 9,198,958 B2
(45) Date of Patent: *Dec. 1, 2015

(54) LYOPHILIZED PREPARATION OF BOTULINUM TOXIN

(71) Applicant: Medy-Tox Inc., Cheongwon-gun (KR)

(72) Inventors: Hyun Ho Jung, Seoul (KR); Gi Hyeok Yang, Chungcheongnam-do (KR); Chang Hoon Rhee, Seoul (KR); Hack Woo Kim, Chungcheongbuk-do (KR); Sung Bum Kim, Chungcheongbuk-do (KR); Seung Hwan Baek, Chungcheongbuk-do (KR)

(73) Assignee: Medy-Tox Inc. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/533,735

(22) Filed: Nov. 5, 2014

(65) Prior Publication Data

US 2015/0064166 A1    Mar. 5, 2015

Related U.S. Application Data

(63) Continuation of application No. 14/008,326, filed as application No. PCT/KR2012/002418 on Mar. 30, 2012, now Pat. No. 8,920,795.

(30) Foreign Application Priority Data

Mar. 31, 2011 (KR) .................. 10-2011-0029577
Mar. 30, 2012 (KR) .................. 10-2012-0033374

(51) Int. Cl.
| | |
|---|---|
| *A61K 38/46* | (2006.01) |
| *A61K 38/43* | (2006.01) |
| *A61K 38/48* | (2006.01) |
| *A61K 9/19* | (2006.01) |
| *A61K 47/02* | (2006.01) |
| *A61K 47/18* | (2006.01) |
| *A61K 47/22* | (2006.01) |
| *A61K 47/26* | (2006.01) |
| *A61K 47/00* | (2006.01) |
| *A61K 47/20* | (2006.01) |

(52) U.S. Cl.
CPC .............. *A61K 38/4893* (2013.01); *A61K 9/19* (2013.01); *A61K 47/00* (2013.01); *A61K 47/02* (2013.01); *A61K 47/183* (2013.01); *A61K 47/20* (2013.01); *A61K 47/22* (2013.01); *A61K 47/26* (2013.01); *C12Y 304/24069* (2013.01)

(58) Field of Classification Search
CPC .... A61K 2300/00; A61K 38/46; A61K 38/43
See application file for complete search history.

(56) References Cited

U.S. PATENT DOCUMENTS

| | | | |
|---|---|---|---|
| 5,756,468 A | 5/1998 | Johnson et al. | |
| 7,829,525 B2 | 11/2010 | Frevert | |
| 8,323,622 B2 | 12/2012 | Kwon et al. | |
| 8,323,666 B2 | 12/2012 | Hunt | |
| 8,617,569 B2 * | 12/2013 | Binder | 424/239.1 |
| 2014/0086900 A1 * | 3/2014 | Jung et al. | 424/94.67 |

FOREIGN PATENT DOCUMENTS

| | | |
|---|---|---|
| KR | 1020060028475 | 3/2006 |
| KR | 1020080052510 | 6/2008 |
| KR | 1020090005963 | 1/2009 |
| WO | WO 2007/041664 | 4/2007 |
| WO | WO 2009/008595 | 1/2009 |

OTHER PUBLICATIONS

International Search Report for WO2012/134240 A3 Oct. 23, 2012.

* cited by examiner

*Primary Examiner* — Karen Cochrane Carlson
*Assistant Examiner* — Natalie Moss
(74) *Attorney, Agent, or Firm* — Ted A. Chan

(57) ABSTRACT

There are provided a lyophilized preparation of botulinum toxin without a protein stabilizer derived from animals. The lyophilized preparation of botulinum toxin according to the present invention can maintain an activity of botulinum toxin, and also exhibit excellent long-term storage stability even under conditions of high temperature, which may occur when botulinum toxin is stored, delivered, and processed.

17 Claims, No Drawings

LYOPHILIZED PREPARATION OF BOTULINUM TOXIN

CROSS-REFERENCE TO RELATED APPLICATION

This application is a continuation of U.S. application Ser. No. 14/008,326, filed Dec. 10, 2013, which is a national stage application under 35 U.S.C. §371 of International Application PCT/KR2012/002418, filed Mar. 30, 2012, which claims priority to, and the benefit of, Korean Patent application No. 2011-0026577, filed on Mar. 31, 2011, and Korean Patent Application No. 2012-0033374, filed on Mar. 30, 2012, the disclosures of each of which are incorporated herein by reference in their entirety.

BACKGROUND

1. Field of the Invention

The present invention relates to a lyophilized preparation of botulinum toxin without a protein stabilizer derived from animals.

2. Discussion of Related Art

Botulinum toxin, which is a polypeptide product of *Clostridium botulinum*, anaerobic bacteria, is a toxic material that specifically affects a nerve cell. Although botulinum toxin originally is a toxic material causing death, in recent years, it is used for treating cervical dystonia, blepharospasm, hyperhidrosis, strabismus, achalasia, neurogenic bladder, urologic disease, migraine, and the like. As an example of use of botulinum toxin as a pharmaceutical composition, there is Meditoxin Inj. being sold by the present inventors now.

Many proteins having a medicinal effect exhibit a property of adhesiveness to a solid surface. Therefore, when the proteins are injected to a container, some of the proteins adhere to an inner wall of the container, thereby causing loss of an active component. In addition, since protein may easily be oxidized or degraded into small fragments, it is necessary to add a stabilizer as a material capable of preventing oxidation and degradation of the protein.

Recently, albumin and gelatin are used as a stabilizer for botulinum toxin. Loss of protein active components may be decreased by reducing protein denaturation caused due to protein adhesion or dilution when albumin is injected into a container. Gelatin is obtained by collagen hydrolysis and sometimes may be used instead of albumin. However, since albumin and gelatin are proteins derived from animals, there is a danger of pathogens derived from blood or latent infection. Therefore, a stabilizer which is not derived from animals and also does not cause activity loss of botulinum toxin is needed.

In this regard, the present inventors disclosed a pharmaceutical liquid composition of botulinum toxin including botulinum toxin, methionine, and polysorbate 20 that exhibits long-term stability at normal temperature in Korean Patent Publication No. 2009-0005963. However, in such a liquid composition, it is difficult to maintain stability of botulinum toxin at a high temperature higher than normal temperature.

SUMMARY OF THE INVENTION

An object of the present invention is to provide a lyophilized preparation of botulinum toxin, in which storage stability can be maintained for a long period of time at a high temperature higher than normal temperature.

For the conventional preparation of botulinum toxin, stability of botulinum toxin can be maintained at a refrigerator temperature or normal temperature. However, it is difficult to maintain an activity of botulinum toxin for a long period of time at a high temperature. Therefore, the present inventors developed a lyophilized preparation of botulinum toxin having excellent storage stability, in which an activity of botulinum toxin can be maintained for a long period of time even across a wide temperature range, for example, a freezing temperature, a refrigerant temperature, normal temperature, and a high temperature.

Therefore, the present invention provides a pharmaceutical lyophilized preparation comprising 1) botulinum toxin; 2) polysorbate; and 3) methionine; and one or more components selected from the group consisting of 4) sugar, sugar alcohol, and an ionic compound.

DETAILED DESCRIPTION OF EXEMPLARY EMBODIMENTS

Hereinafter, the present invention will be described in detail with reference to examples and comparative examples. However, the present invention is not limited to these examples.

The lyophilized preparation of botulinum toxin according to the present invention comprises 1) botulinum toxin, 2) polysorbate, and 3) methionine, which have been added to the conventional liquid preparation; and further includes one or more selected from the group consisting of 4) sugar, sugar alcohol, and an ionic compound as an additional component.

The additional component functions as maintaining an activity of botulinum toxin, and also stabilizing the activity even at a high temperature higher than normal temperature when bolulinum toxin is prepared in a form of a lyophilized formulation. For a composition including 1) botulinum toxin; 2) polysorbate; and 3) methionine, its stability decreases when being lyophilized, and also decreases at a high temperature higher than normal temperature even when prepared in a liquid preparation. However, the lyophilized preparation of botulinum toxin according to the present invention can maintain the activity of botulinum toxin even at a high temperature higher than normal temperature, and also can have excellent long-term storage stability.

The botulinum toxin which is included in the lyophilized preparation according to the present invention may be derived from *Clostridium botulinum*. The botulinum toxin which is included in the lyophilized preparation according to the present invention may be isolated and purified from those strains through known methods, or commercially available products may be used as the botulinum toxin.

The botulinum toxin which is included in the lyophilized preparation according to the present invention may be any selected from the group consisting of Botulinum Serotypes A, B, C, D, E, F, and G. The botulinum toxin is divided into Serotypes A, B, C, D, E, F, and G according to an immunological distinguishing method. It is known that the botulinum toxins of all Serotypes inhibit a secretion of acetylcholine, which is a signaling molecule in a neuromuscular junction, thereby generating an effect of neural paralysis, and different Serotypes may affect different animal species and have different degrees of paralysis, durations, and the like.

Meanwhile, when a toxin protein is produced by *Clostridium botulinum*, the botulinum toxin protein is produced by forming various complexes with various hemagglutinine proteins and non-hemagglutinine proteins, which assist and protect a function of botulinum toxin protein. The botulinum toxin which is included in the lyophilized preparation according to the present invention may include a complex form with a complexing protein and a form without a complexing protein. The activity of botulinum toxin is unaffected by whether or not the complexing protein is included.

In the lyophilized preparation of botulinum toxin according to the present invention, polysorbate, which is one of stabilizers of botulinum toxin, is a nonionic surfactant and mainly used as an emulsifying agent in the field of pharmaceuticals or food. A type of polysorbate includes polysorbates 20, 40, 60, 80, and 100 on the basis of the total number of an oxyethylene group. For the lyophilized preparation of botulinum toxin according to the present invention, all of those polysorbates can be used. The polysorbate may be included in an amount of 0.01 to 2 mg with respect to 100 units of botulinum toxin. Within the above range, an activity of botulinum toxin can be maintained even at a high temperature higher than normal temperature, and also storage stability can be maintained for a long period of time.

In addition, methionine, a stabilizer, is used instead of an animal protein such as albumin and gelatin as a stabilizer of botulinum toxin. Methionine may be included in an amount of 0.01 to 10 mg with respect to 100 units of botulinum toxin. Within the above range, an activity of botulinum toxin can be maintained even at a high temperature higher than normal temperature, and also storage stability can be maintained for a long period of time.

The lyophilized preparation of botulinum toxin according to the present invention further includes at least one of 4) sugar, sugar alcohol, or an ionic compound as an additional component in addition to methionine and polysorbate, unlike the conventional liquid preparation.

Sugar is known to prevent denaturation of macromolecules. An example of sugar that may be used for the lyophilized preparation according to the present invention includes, but is not limited to, trehalose, sucrose, maltose, fructose, raffinose, lactose, glucose, or the like. Such sugar may be included in an amount of 0.1 to 50 mg with respect to 100 units of botulinum toxin. Within the above range, an activity of botulinum toxin can be maintained even at a high temperature higher than normal temperature, and also storage stability can be maintained for a long period of time.

Sugar alcohol is known to stabilize macromolecules when freeze-dried or in a liquid state, and to prevent denaturation. An example of sugar alcohol that may be used for the lyophilized preparation according to the present invention includes, but is not limited to, cyclodextrin, mannitol, sorbitol, glycerol, xylitol, inositol, or the like. The sugar alcohol may be included in an amount of 0.1 to 50 mg with respect to 100 units of botulinum toxin. Within the above range, an activity of botulinum toxin can be maintained even at a high temperature higher than normal temperature, and also storage stability can be maintained for a long period of time.

In addition, an ionic compound means salt or a buffer. An ionic compound reacts with macromolecules through specific or non-specific binding. The salt may increase thermostability and solubility, and may decrease a degree of aggregation. However, it is important to note that a protein may tend to be denatured at a high concentration of salt. An example of the ionic compound includes, but is not limited to, sodium chloride, sodium phosphate, ammonium phosphate, magnesium sulfate, sodium acetate, sodium lactate, sodium succinate, sodium propionate, potassium phosphate, or the like. The ionic compound may be included in an amount of 0.1 to 10 mg with respect to 100 units of botulinum toxin. Within the above range, an activity of botulinum toxin can be maintained even at a high temperature higher than normal temperature, and also storage stability can be maintained for a long period of time.

The lyophilized preparation of botulinum toxin according to the present invention is prepared from a culture of *Clostridium botulinum* cultured in a specific medium, but the present invention is not limited thereto. A complex of botulinum toxin is purified from the culture solution through a series of acid precipitations to obtain a crystal complex of botulinum toxin composed of an active high-molecular weight toxin protein and a relevant haemagglutinin protein. The crystal complex is dissolved in a solution including salt water and a stabilizer, and then freeze-dried to produce the lyophilized preparation of botulinum toxin.

The lyophilized preparation of botulinum toxin according to the present invention can maintain an activity of botulinum toxin, and also exhibit excellent long-term storage stability even under conditions of high temperature, which may occur when botulinum toxin is stored, delivered, and processed.

The present invention can be used as a medicine for treating cervical dystonia, blepharospasm, hyperhidrosis, strabismus, achalasia, neurogenic bladder, urologic disease, migraine, and the like.

The advantages and characteristics of the present invention, and methods for obtaining the advantages and characteristics of the present invention, will be apparent with reference to the exemplary embodiments described in detail below. However, the present invention is not limited to any aspect of the exemplary embodiments disclosed below and may be implemented in various different forms. The exemplary embodiments are only provided to enable those skilled in the art to embody and practice the present invention. The technical spirit and scope of the present invention is defined by the appended claims.

EXAMPLE 1

Production of Lyophilized Preparation of Botulinum Toxin

A lyophilized preparation of botulinum toxin according to the present invention was prepared by lyophilizing (or freeze-drying) g a sterilized preparation solution including botulinum toxin, methionine, and polysorbate, and sugar or sugar alcohol and/or an ionic compound.

(Botulinum Toxin Stability Test)

Stability of botulinum toxin was determined by confirming continuity of activity after storing for a certain period of time and the continuity of activity of botulinum toxin was measured by checking a lethality of mice or mouse $LD_{50}$. A dosage form of the lyophilized preparation was stored at 40° C. and a relative humidity of 70% for 30 days and then dissolved in physiological saline. Then, the botulinum toxin corresponding 2.5 $LD_{50}$ IU was abdominally injected to three mice. When two or more mice died, it was determined that stability continued, which is expressed as mortality in the following Table. When the mice mortality is 50% or more, it may be estimated that activity of botulinum toxin is maintained.

(Titrimetry)

A titrimetry was performed as follows. 2.8 mL of physiological saline was added to two vials including specimens, respectively. 4.4 mL of the specimen was taken from the vial, and then 1.45 mL of physiological saline was added to the specimen to obtain a Test solution 1. 1.45 mL of physiological saline was added to 4.4 mL of Test solution 1 to obtain a Test solution 2. By the same method, dilution of the solution was repeatedly performed eight times to obtain each of the test solutions. For Test solutions 3 to 6, 0.1 mL of each of the test solutions was abdominally injected to 10 mice (CD1, female)

having a weight of 17 to 22 g, and then after 3 days, a lethality was measured. The results were statistically processed by using a Probit method to obtain mouse $LD_{50}$ and titer.

EXAMPLE 2

Selection of Stabilizer of Botulinum Toxin (1) Selection of Combination of Methionine and Polysorbate In the combination of human serum albumin and polysorbate, which are components of a conventionally known stabilizer of botulinum toxin, a stabilizer for the exchange of the human serum albumin was selected.

TABLE 1

| Composition of liquid formulation | | | Mortality after |
|---|---|---|---|
| Polysorbate 20 (mg/mL) | Botulinum toxin (unit/mL) | Stabilizer (Concentration) | storing for 30 days (%) |
| 2 | 100 | — | 0 |
| | | HSA (5 mg/mL) | 100 |
| | | L-methionine (20 mM) | 100 |
| | | L-arginine (50 mM) | 0 |
| | | Histidine (10 mM) | 0 |
| | | Mannitol (50 mg/mL) | 0 |
| | | Sorbitol (50 mg/mL) | 0 |
| | | Sucrose (50 mg/mL) | 0 |
| | | Lactose (50 mg/mL) | 0 |

From the above results, it was estimated that the combination of HSA and polysorbate 20 could be replaced with the combination of methionine and polysorbate 20 as a stabilizer.

Next, for the combination of methionine and polysorbate 20 selected as a stabilizer of botulinum toxin, stability tests of botulinum toxin were performed according to various concentration changes of methionine and polysorbate 20.

Table 2 shows stability test results (mortality (%)) of botulinum toxin under conditions of various concentrations of methionine and polysorbate 20 in the case of storing for 30 days, and Table 3 shows stability test results (mortality (%)) of botulinum toxin under conditions of various concentrations of methionine and polysorbate 20 in the case of storing for 60 days. The concentration of botulinum toxin in the botulinum toxin liquid composition of the above test was 100 units/mL.

TABLE 2

| | | Methionine (mM) | | | | | |
|---|---|---|---|---|---|---|---|
| Concentration | | 1 | 5 | 10 | 25 | 50 | 75 | 100 |
| Polysorbate 20 (mg/mL) | 0.1 | 100 | 100 | 80 | 100 | 100 | 100 | 100 |
| | 0.5 | 100 | 100 | 80 | 100 | 100 | 100 | 100 |
| | 2.5 | 100 | 100 | 100 | 100 | 100 | 100 | 100 |
| | 10 | 100 | 100 | 100 | 100 | 100 | 100 | 100 |
| | 20 | 100 | 100 | 100 | 100 | 100 | 100 | 100 |
| | 25 | 80 | 100 | 100 | 80 | 80 | 100 | 100 |

TABLE 3

| | | Methionine (mM) | | | | | |
|---|---|---|---|---|---|---|---|
| Concentration | | 1 | 5 | 10 | 25 | 50 | 75 | 100 |
| Polysorbate 20 (mg/mL) | 0.1 | 100 | 100 | 80 | 100 | 100 | 80 | 100 |
| | 0.5 | 100 | 100 | 80 | 100 | 100 | 100 | 100 |
| | 2.5 | 100 | 100 | 100 | 80 | 100 | 100 | 100 |
| | 10 | 0 | 40 | 0 | 100 | 100 | 100 | 40 |
| | 20 | 0 | 80 | 80 | 100 | — | 100 | 60 |
| | 25 | 0 | 0 | 0 | 0 | 80 | — | 0 |

As a result of performing a statistical analysis using the results listed in Tables 2 and 3, it was assumed that the combination of 25 to 75 mM of methionine and 0.1 to 2.5 mg/mL of polysorbate 20 maximally stabilized the botulinum toxin.

(2) Selection of Additional Component

When the methionine and polysorbate 20 selected from Tables 2 and 3 were used as a lyophilized preparation, the contents of methionine and polysorbate 20 were calculated to be in the ranges of 0.01 to 10 mg and 0.01 to 1 mg, respectively. However, when the stabilizer having such a combination was used as the lyophilized preparation, the stability was not maintained after storing for 30 days. Therefore, an additional stabilizer capable of maintaining the stability was selected, as listed in Table 4. At this time, 100 units of botulinum toxin, 3 mg of methionine, and 2 mg of polysorbate 20 were used.

TABLE 4

| Composition of lyophilized preparation | | | | | | |
|---|---|---|---|---|---|---|
| | Additional stabilizer | | | | | Mortality after |
| | Sodium chloride | Sodium phosphate | Sucrose | Mannitol | Sorbitol | storing for 30 days (%) |
| Botulinum toxin + Methionine + Polysorbate 20 | — | — | — | — | — | 0 |
| | 0.9 mg | — | — | — | — | 100 |
| | — | 10 mM | — | — | — | 100 |
| | — | — | 0.3 mg | — | — | 100 |
| | — | — | — | 40 mg | — | 100 |
| | 0.9 mg | — | — | 40 mg | — | 100 |
| | — | 10 mM | — | 40 mg | — | 100 |
| | — | 10 mM | 50 mg | — | — | 100 |
| | 0.9 mg | — | 50 mg | — | — | 100 |
| | — | 10 mM | 50 mg | — | 40 mg | 100 |

As shown in Table 4, it could be confirmed that when the lyophilized preparation including only methionine and polysorbate as a stabilizer was used, the stabilization effect of botulinum toxin was not maintained, but when at least one of sugar, sugar alcohol, and an ionic compound was further added in addition to methionine and polysorbate, the stabilization effect was maintained.

Next, a proper content and a type of sugar, sugar alcohol, or an ionic compound which is further added to the combination of methionine and polysorbate were tested. At this time, 100 units of botulinum toxin, 2 mg of methionine, and 0.2 mg of polysorbate 20 were used.

TABLE 5

| Composition of lyophilized preparation | | | Mortality after storing for |
|---|---|---|---|
| | Additional stabilizer | Content | 30 days (%) |
| Botulinum toxin + Methionine + Polysorbate 20 | Sucrose | 0.3 mg | 100 |
| | | 2.0 mg | 100 |
| | | 4.0 mg | 100 |
| | | 50 mg | 100 |
| | Trehalose | 0.3 mg | 100 |
| | | 2.0 mg | 100 |
| | Sorbitol | 40 mg | 100 |

TABLE 5-continued

| Composition of lyophilized preparation | | | Mortality after storing for |
|---|---|---|---|
| | Additional stabilizer | Content | 30 days (%) |
| | Mannitol | 40 mg | 100 |
| | Sodium chloride | 0.06 mg | 0 |
| | | 0.1 mg | 100 |
| | | 0.3 mg | 100 |
| | | 0.6 mg | 100 |
| | | 0.9 mg | 100 |
| | | 1.2 mg | 100 |
| | | 10 mg | 100 |
| Sodium phosphate | sodium hydrogen phosphate, anhydrous | 0.05 mg | 100 |
| | Sodium dihydrogen phosphate dihydrate | 0.101 mg | |

As shown in Table 5, it could be confirmed that when 0.1 to 50 mg of sucrose and 0.1 to 10 mg of sodium chloride were added to the combination of methionine and polysorbate, the stabilization effect was maintained. When the content of the additional stabilizer was the above range or less, there was no stabilization effect, while when the content of the additional stabilizer was the above range or more, the stable type as the lyophilized preparation was not obtained.

Next, the long-time stability test of the lyophilized preparation at a high temperature was performed by using titrimetry. At this time, when the combination of botulinum toxin+methionine+polysorbate 20+sodium phosphate+sucrose was used as the lyophilized preparation, 100 units of botulinum toxin, 0.8 mg of methionine, 0.02 mg of polysorbate 20, sodium phosphate (0.05 mg of sodium hydrogen phosphate, anhydrous+0.101 mg of sodium dihydrogen phosphate dehydrate), and 4 mg of sucrose were used. When the combination of botulinum toxin+methionine+polysorbate 20+sodium chloride+sucrose was used as the lyophilized preparation, 100 units of botulinum toxin, 0.2 mg of methionine, 0.02 mg of polysorbate 20, 2 mg of sodium chloride, and 4 mg of sucrose were used. When the lyophilized preparation including human serum albumin was used as a control group, 0.5 mg of human serum albumin and 0.9 mg of sodium chloride were used.

TABLE 6

| | Titer (units) | | | | | |
|---|---|---|---|---|---|---|
| Composition of lyophilized preparation | 0 week titer | 2 weeks titer | 4 weeks titer | 8 weeks titer | 12 weeks titer | 24 weeks titer |
| Botulinum toxin + Human serum albumin + Sodium chloride | — | 0 | 0 | — | — | — |
| Botulinum toxin + Methionine + Polysorbate 20 + Sodium phosphate (Sodium chloride) + Sucrose | 109 (120) | 100 (95) | 80 (95) | 100 (120) | 95 | 103 |

As shown in Table 6, it could be confirmed that when the combination of botulinum toxin, methionine, polysorbate, sodium phosphate or sodium chloride, and sucrose was used as the lyophilized preparation, the stabilization effect was maintained for about 6 months.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A pharmaceutical lyophilized preparation comprising: botulinum toxin, polysorbate, and methionine; and one or more components selected from the group consisting of sugar, sugar alcohol, and an ionic compound, wherein the preparation is free of albumin, and wherein stability of the botulinum toxin is maintained for at least 30 days at 40° C. and 70% relative humidity.

2. The pharmaceutical lyophilized preparation of claim 1, wherein the stability of the botulinum toxin is maintained for 6 months.

3. The pharmaceutical lyophilized preparation of claim 1, wherein the botulinum toxin is selected from the group consisting of Botulinum Serotypes A, B, C, D, E, F, and G.

4. The pharmaceutical lyophilized preparation of claim 1, wherein the botulinum toxin is a form without a complexing protein or a complex form with a complexing protein.

5. The pharmaceutical lyophilized preparation of claim 1, wherein the polysorbate is any one of polysorbates 20, 40, 60, 80, and 100.

6. The pharmaceutical lyophilized preparation of claim 1, wherein the polysorbate is included in an amount of 0.01 to 2 mg with respect to 100 units of the botulinum toxin.

7. The pharmaceutical lyophilized preparation of claim 1, wherein the methionine is included in an amount of 0.01 to 10 mg with respect to 100 units of the botulinum toxin.

8. The pharmaceutical lyophilized preparation of claim 1, wherein the sugar is one or more selected from the group consisting of trehalose, sucrose, maltose, fructose, raffinose, lactose, and glucose.

9. The pharmaceutical lyophilized preparation of claim 1, wherein the sugar is included in an amount of 0.1 to 50 mg with respect to 100 units of the botulinum toxin.

10. The pharmaceutical lyophilized preparation of claim 1, wherein the sugar alcohol is one or more selected from the group consisting of cyclodextrin, mannitol, sorbitol, glycerol, xylitol, and inositol.

11. The pharmaceutical lyophilized preparation of claim 1, wherein the sugar alcohol is included in an amount of 0.1 to 50 mg with respect to 100 units of the botulinum toxin.

12. The pharmaceutical lyophilized preparation of claim 1, wherein the ionic compound is one or more selected from the group consisting of sodium chloride, sodium phosphate, ammonium phosphate, magnesium sulfate, sodium acetate, sodium lactate, sodium succinate, sodium propionate, and potassium phosphate.

13. The pharmaceutical lyophilized preparation of claim 1, wherein the ionic compound is included in an amount of 0.1 to 10 mg with respect to 100 units of the botulinum toxin.

14. A pharmaceutical lyophilized preparation comprising:
   botulinum toxin, polysorbate, methionine, sugar, and an ionic compound,
wherein the preparation is free of albumin, and
wherein stability of the botulinum toxin is maintained for at least 30 days at 40° C. and 70% relative humidity.

15. The pharmaceutical lyophilized preparation of claim 14, wherein the stability of the botulinum toxin is maintained for 6 months.

16. A pharmaceutical lyophilized preparation comprising:
   botulinum toxin, polysorbate 20, methionine, sucrose, and sodium chloride,
wherein the preparation is free of albumin, and
wherein stability of the botulinum toxin is maintained for at least 30 days at 40° C. and 70% relative humidity.

17. The pharmaceutical lyophilized preparation of claim 16, wherein the stability of the botulinum toxin is maintained for 6 months.

* * * * *